United States Patent [19]

Payne et al.

[11] Patent Number: 4,887,455
[45] Date of Patent: Dec. 19, 1989

[54] GAS SENSOR

[75] Inventors: Peter A. Payne; Jon G. Bartlett, both of Manchester; Natalie K. Harris, Cornwall, all of England

[73] Assignee: Cogent Limited, London, England

[21] Appl. No.: 177,671

[22] Filed: Apr. 5, 1988

[30] Foreign Application Priority Data

Apr. 6, 1987 [GB] United Kingdom ............... 8708201

[51] Int. Cl.$^4$ ............................................. G01N 27/02
[52] U.S. Cl. ................................. 73/27 R; 324/65 R
[58] Field of Search ............... 73/23, 27 R; 324/65 R, 324/65 D; 357/25; 422/96

[56] References Cited

U.S. PATENT DOCUMENTS

| | | | |
|---|---|---|---|
| 3,621,343 | 11/1971 | Pulvari et al. | 324/61 R |
| 4,103,227 | 7/1978 | Zemel | 73/23 |
| 4,140,990 | 2/1979 | DeWarren | 324/71.1 |
| 4,453,126 | 6/1984 | Volgyesi | 324/65 R |
| 4,674,319 | 6/1987 | Muller | 73/23 |
| 4,681,855 | 7/1987 | Huang | 73/23 |
| 4,721,601 | 1/1988 | Wrighton et al. | 422/68 |

FOREIGN PATENT DOCUMENTS 8601599 3/1986 World Int. Prop. O. .

OTHER PUBLICATIONS

T. Maruizumi et al., "A.C. Impedance Study on Chloride Ion Sensitive Polymeric Membranes", undated.
El Kadiri et al., "Frequency and Temperature-Dependent Complex Conductivity of Some Conducting Polymers", undated.
Yuequiang et al., "Structure and Conductivity of Some Heavily Doped Polypyrroles", undated.

Primary Examiner—Hezron E. Williams
Attorney, Agent, or Firm—Larson and Taylor

[57] ABSTRACT

A gas sensor has a layer of a semiconductor organic polymer, such as polypyrrole which is exposed to a gas to be detected. An alternating electric signal of varying frequency is applied to the sensor by an analyser, which detects the change in impedance characteristics of the sensor. The characteristics obtained are compared by microcomputer with reference characterisitcs stored in a memory. The resulting difference spectra depend on the gas in contact with the sensor and so the gas can be detected.

6 Claims, 8 Drawing Sheets

GAS SENSOR

BACKGROUND OF THE INVENTION

1. Field of the Invention

This invention relates to gas sensors. In this specification the term "gas" refers to materials which are normally gaseous, and also to vapours and odours.

There are many circumstances in which it is desired to detect specific gas or gases in an environment; for example, the emission of certain gases from foodstuffs indicating their condition, the presence of certain pollutants in the atmosphere, or the presence of anaesthetic gases in hospital operating rooms and dental surgeries.

2. Summary of the Prior Art

The semiconduction property of polypyrrole has been used for gas detection, but only to a limited extent. Nylander et al (Nylander, C., Armagathi, M. and Lundstrom, I.) Anal. Chem. Symp Series, 1983, 1 203–207 detected ammonia using a sensing element of precipitated pyrrole black on a filter paper substrate. An almost linear DC resistance change response was obtained with high concentrations of ammonia. The device was also sensitive to moisture and to anions. Maisik et al (Maisik, J. J., Hooper, A. and Tofield, B. C.) JCS Faraday Trans. I, 1986, 82, 1117-26 demonstrated a polypyrrole gas sensor using electrochemically prepared films or interdigitated electrodes. They showed that polypyrrole is in fact sensitive to nitrous oxide and hydrogen sulphide. Pelosi and Persaud (Pelosi, P. and Persaud, K. C.) PCT Int. Appln. WO086/01599, 1986 reported on the sensitivity of a number of semiconducting organic polymers to organic vapours and gases. Such polymers included polypyrrole, poly-2-chloroaniline, poly-2-acetonitrile, polyindole and poly-2-isobutylthiazole. The vapours or gases produced changes in DC resistance in various of the polymers. A major problem in utilising the above phenomena is that of obtaining a signal which can be regarded as specific to a particular gas under investigation.

SUMMARY OF THE INVENTION

The present invention is based on the discovery of changes in the AC impedance characteristics of a semiconducting organic polymer such as polypyrrole at particular frequencies in the presence of a gas. It is found that there is a significant variation in impedance characteristics (conductance characteristic and/or susceptance characteristic) and the variation is different from gas to gas.

It may be possible to detect particular gases by investigating changes in the impedance characteristics localised at particular frequencies. However, it has been found that some of the variations are due to noise, and therefore it is difficult reliably to detect particular gases from any localised change in the impedance characteristics at particular frequencies.

It is evident, however, that different gases impose a different overall variation function on the impedance characteristics of polymer. Therefore it is preferable to use a comparison system in which the variation of impedance characteristics are determined over a range of frequencies for a reference gas (such as nitrogen or dry air) and that reference variation is compared with the variation for other gases. By subtracting the reference variation from the variation due to the gas to be detected, difference functions are obtained for the impedance characteristics which functions differ depending on the gas to be detected.

The variations in impedance characteristics are most apparent at high frequencies e.g. greater than 1 MHz. Therefore, the investigation of the variation is normally over a 1 MHz to 500 MHz range.

The theoretical reason for the variation in impedance characteristics is not fully understood. It is thought (although this should not be considered limiting of the present invention) that gas molecules are adsorbed onto the polymer, there is a localised change in shape of the polymer molecule and this causes a variation in the impedance.

Although most of the investigations of semiconducting organic polymers have concentrated on polypyrrole, it is expected that similar variations will also occur with other semiconducting organic polymers such as poly-2-chloroaniline, poly-2-acetonitrile, polyindole and poly-2-isobutylthiazole.

Thus a gas detector may comprise a number of sensors incorporating different polymers, each reacting individually to gases and building up a composite picture of the component gas or gases. Furthermore, such different polymers can be superimposed in a multilayer (two or more layers) structure, whereby the characteristics of a base layer such as polypyrrole are modified by the deposition on its surface of one or more layers of other semiconducting polymers. Combinations of semiconducting polymers can be achieved also with the same basic polymer, such as polypyrrole, but made in different ways, such as with different dopants, so as to provide different changes in AC impedance characteristics.

In a particular case, a sensor comprises p-type doped polypyrrole bridging a pair of electrodes, and measurements of conductance and susceptance of the polypyrrole at a spectrum of frequencies are used to detect the presence of halothane. By previously calibrating the sensor with a standard gas (such as $N_2$ or dry air), difference spectra can be determined, and these spectra thereafter applied to the sensor in use; and also the sensitivity of the sensor can be calibrated so that the observed signals in use can give an indication of the concentration of gas present.

BRIEF DESCRIPTION OF THE DRAWINGS

In order that the invention may be more clearly understood, one embodiment will now be described with reference to the accompanying drawings, wherein.

DETAILED DESCRIPTION

Figure 1:
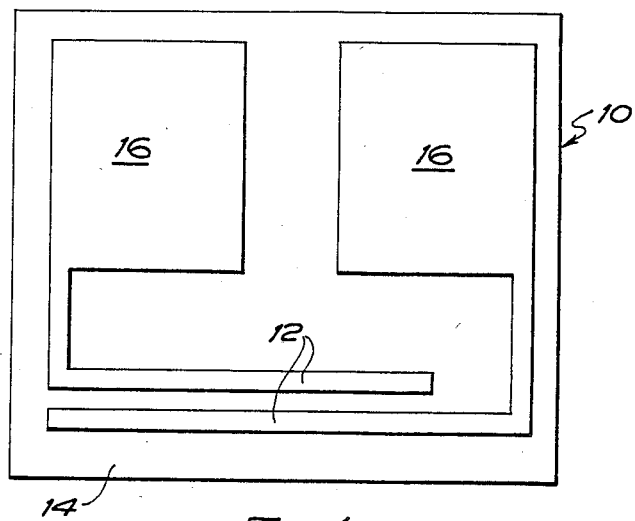
FIG. 1 is a plan view, greatly enlarged, of the sensor used in the tests.

As shown in FIG. 1, the sensor 10 comprised a pair of gold electrodes 12 deposited on a non-conductive silica substrate 14. Each electrode 12 extended to a contact area 16 for connection to an electrical lead. The working portions of the electrodes comprises a pair of parallel strips each 7 mm long × 250 μm wide and about 1 μm thick, spaced apart by 250 μm.

Figure 2:
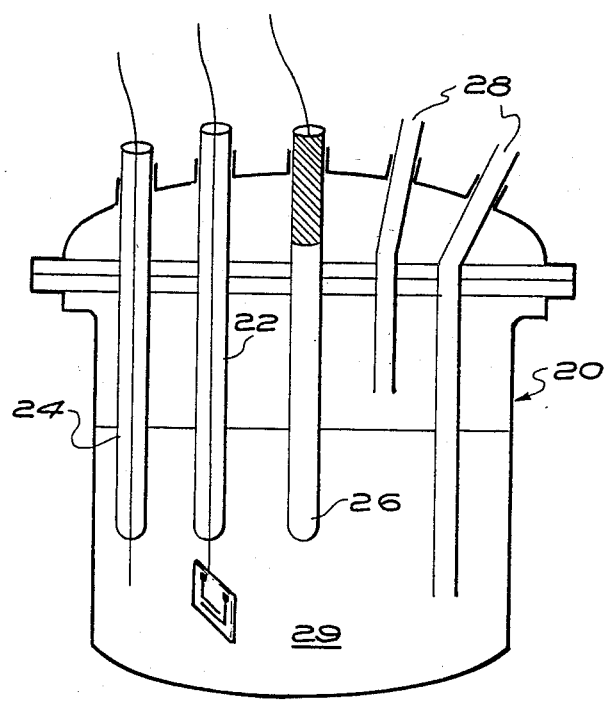
FIG. 2 is a diagrammatic side view of an electrolytic cell for depositing polypyrrole on the sensor.

The electrodes were coated with polypyrrole using known procedures, (see e.g. Kanazawa, K. K., Diaz, A. F., Geiss, R. H., Gill, W. D., Kwak, J. F., Logan, J. A., Rabolt, J. and Street, G. B. JCS Chem. Comm., 1979, 854–855 or Diaz, A. F. Chem. Ser. 17, 1981, 145–148), by electrolytic oxidation of polypyrrole monomer in an electrochemical cell 20 as shown in FIG. 2. The sensor was connected to the anode 22 of the cell, which has a cathode 24, a standard calomel reference electrode 26, and was flushed with nitrogen through ports 28. The electrolyte comprised 60 mM pyrrole and 0.1M tetraethylammonium-tetrafluoroborate or 0.1M tetraethylammonium p-toluene sulphonate (the p-type dopant) in a 99% acetonitrile/1% water medium. The anode was at 1 V with respect to the reference electrode 26. At the end of the polymerisation the sensor were washed in acetonitrile and dried in a flow of nitrogen.

Figure 3:
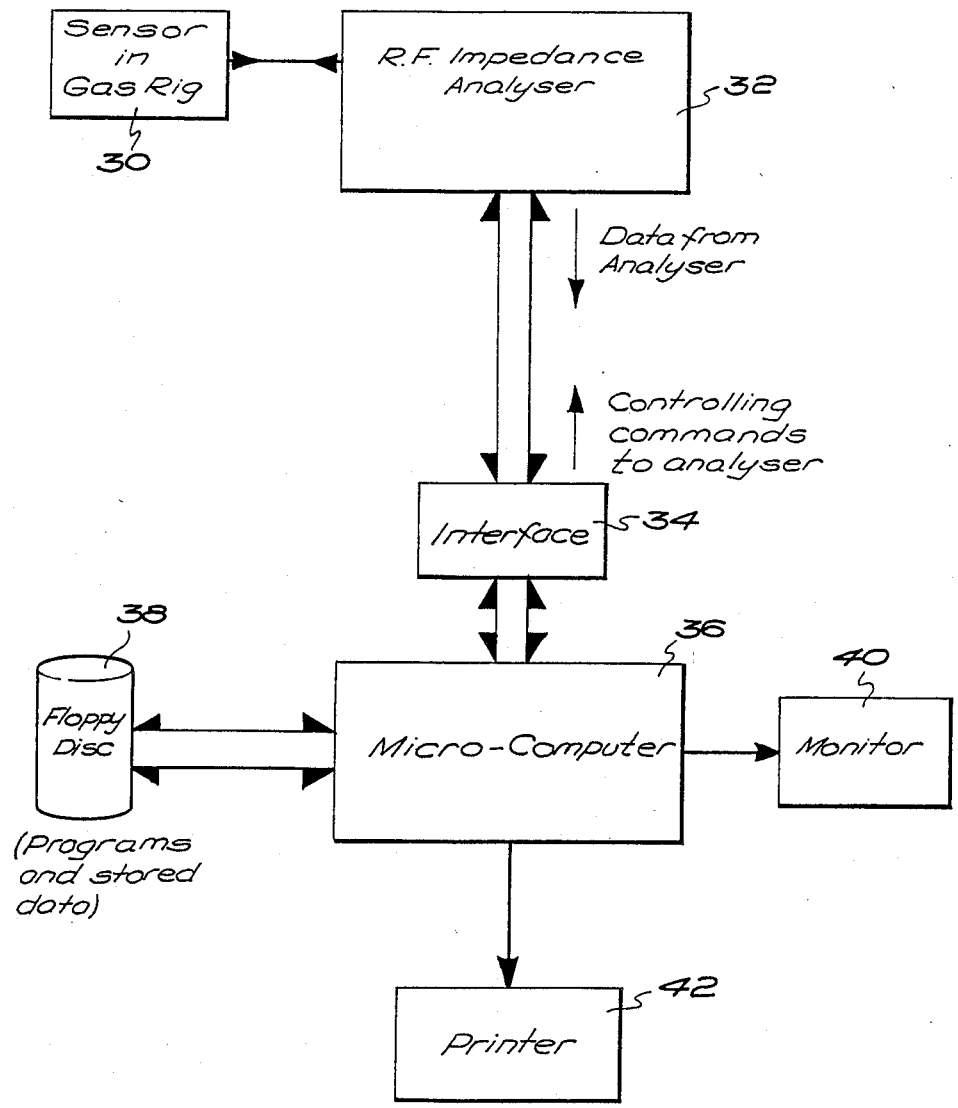
FIG. 3 is a block diagram of experimental apparatus used to operate the sensor.

The conductance G and the susceptance B values of the electrode were measured over a range of frequencies, typically from 1–500 MHz, using a Hewlett Packard 4191A RF impedance analyser, as part of an experimental apparatus which is shown in block form in FIG. 3. The sensor was placed in a gas rig 30, which enabled the user to vary the exposure of the sensor between a control gas and the test gas. The control gas providing the standard environment was dry nitrogen because of its inert properties. The test gas halothane was introduced at a concentration of 1000 ppm. The sensor was connected to the RF impedance analyser 32, which was connected through an intelligent interface 34 (CCS IEEE 488) to a microcomputer 36 (Amstrad PC1512). The programs and data were stored in a memory e.g. a disk 38, and the computer was also connected to a monitor 40 (if desired) and printer 42. Programs were written for the computer, inter alia to calculate difference spectra; i.e. to compare the conductance and susceptance measurements over a given frequency range in the presence of a specified test gas with the corresponding responses over the same frequency range produced in the presence of only the control gas. The program also allowed the absolute response to be recorded.

Figure 4:
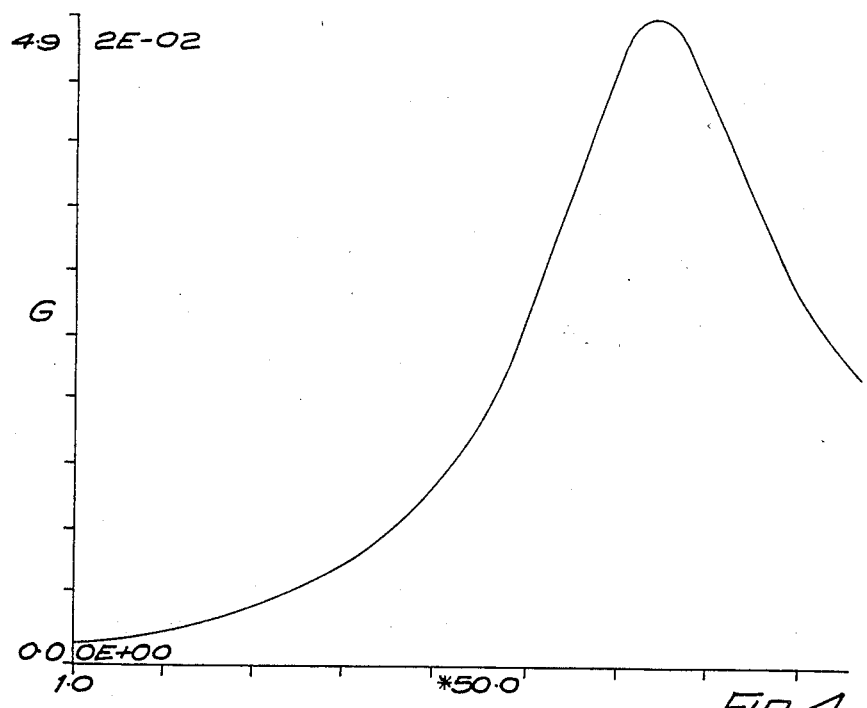
FIGS. 4 and 5 show typical conductance and susceptance traces for the electrode in the presence of $N_2$.
Figure 5:
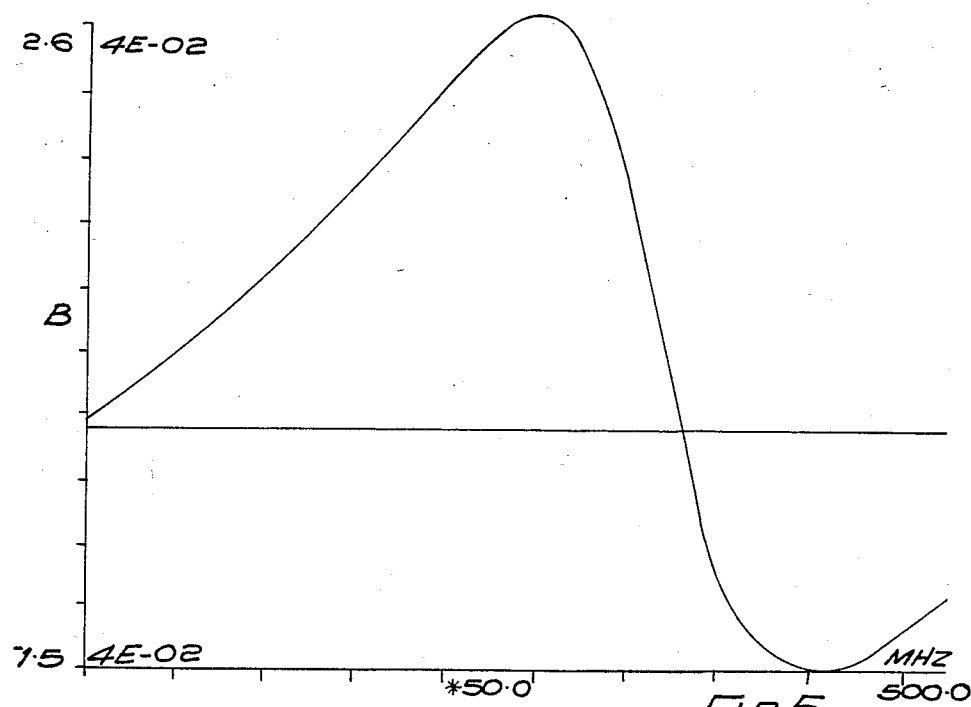
Figure 6:
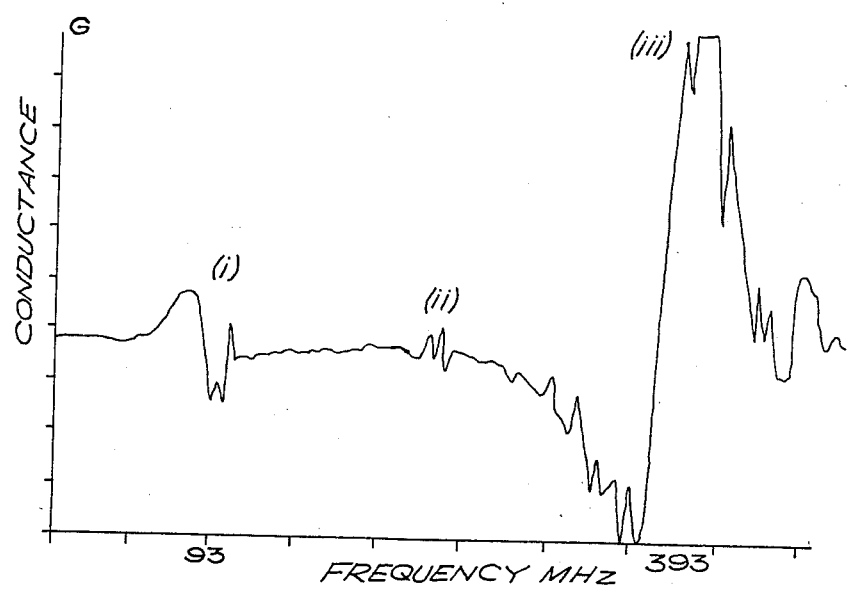
FIGS. 6 and 7 show the difference spectra of the sensor for conductance and susceptance respectively, in presence of halothane.
Figure 7:
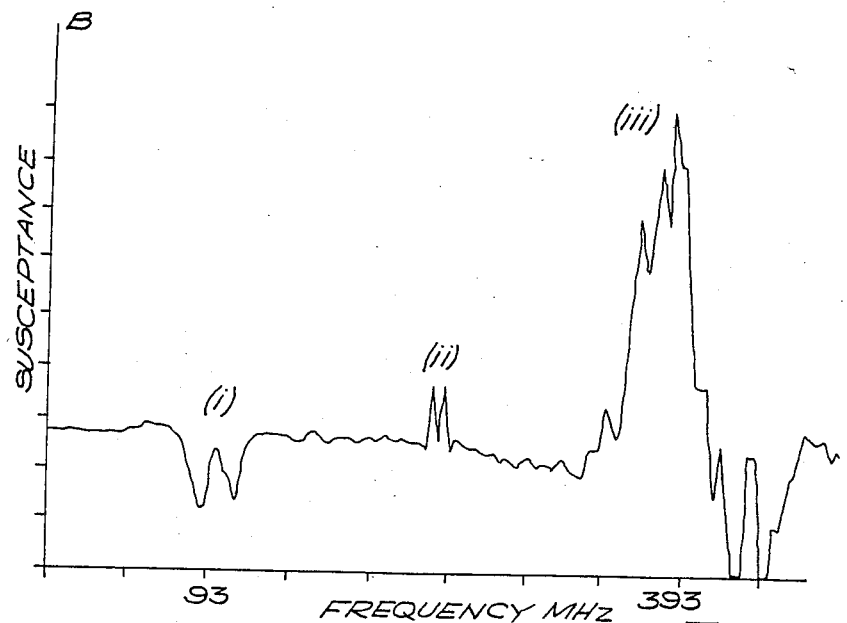

Typical conductance and susceptance measurements over a range of frequencies from 1–500 MHz was taken in the presence of the standard gas (nitrogen) only, and the data stored on the floppy disk. The traces are shown in FIGS. 4 and 5. Then, in the presence of 1000 ppm halothane, the conductance and susceptance measurements were taken again and compared with the stored data on the floppy disk, and the differences between the two spectra were measured. The resulting traces are shown in FIGS. 6 and 7 for conductance and susceptance respectively.

The conductance difference trace (FIG. 6) shows an overall function with a prominent trough around 337 MHz, whereas the susceptance trace shows a difference spectrum with a peak and trough symmetrical about 340 MHz. Abberations localised in frequency may be observed e.g. at (i), (ii), (iii), but in general such variations are thought to be due to noise, rather than due to the halothane, but overall functions suggesting that the halothane a "gas transfer function" modifying the impedance spectra rather than being additive to the absolute impedance of the sensor.

Comparing the difference spectra to the sensor's absolute conductance and susceptance traces, it can be seen that in the case of conductance, the largest deviation (trough at 337 MHz) occurs at a slightly increased frequency from the resonant peak. The susceptance trace is also shifted. This shift is explained by a decrease in resonant frequency on the introduction of halothane to the sensor. The halothane interaction can be expected to give a shift in this resonant frequency as the gas is thought to be adsorbed by the film, altering the dielectric properties of the polymer. A change in the overall (dc) resistivity is also expected due to a change in the number of charge carriers in the semiconducting film. These two effects are expected to produce a broader, slightly shifted conductance peak with a minimal change in height. However, these two effects would produce conductance difference traces that were symmetrical about a frequency between the standard and shifted resonant peaks.

The non-symmetrical conductance trace suggests that the "gas transfer function" has a second order frequency dependent term. This may be a result of a concentration profile of the adsorbed gas in the film affecting the conductance as a function of electrical skin depth. As the frequency of the impedance interrogation signal rises, an increasing proportion of the current is transmitted near the surface of the polymer film and is therefore more readily accessible to, and influenced by, the changes in the film composition near the surface. This is called the skin effect. The "skin depth" is the depth from the surface at which the current has dropped to 1/e (36%) of its value at the surface. Skin depth is therefore a function of the applied high frequency measurement signal.

Figure 8:
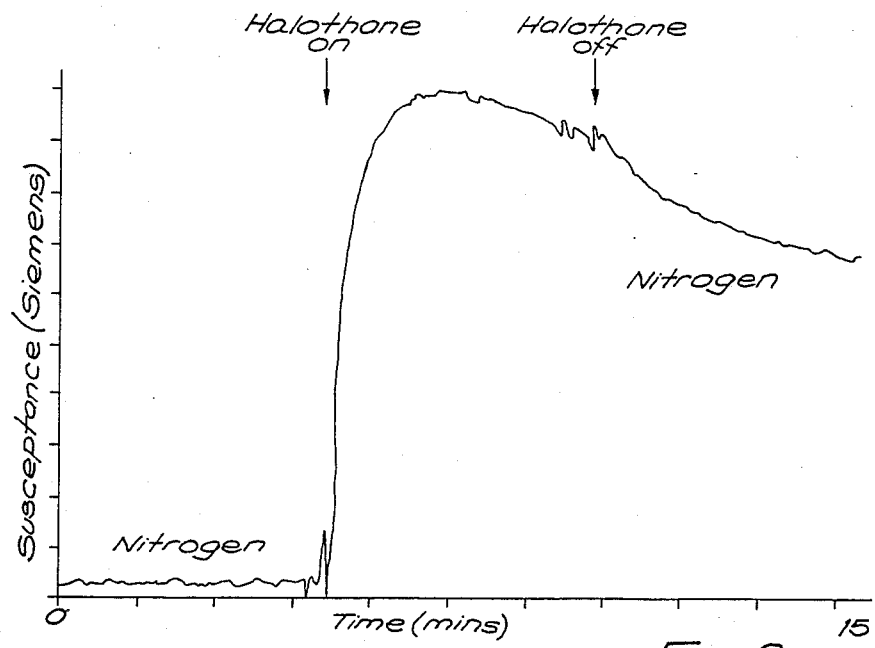
FIG. 8 shows the susceptance response of the sensor to 1000 ppm halothane at 393 MHz.
Figure 9:
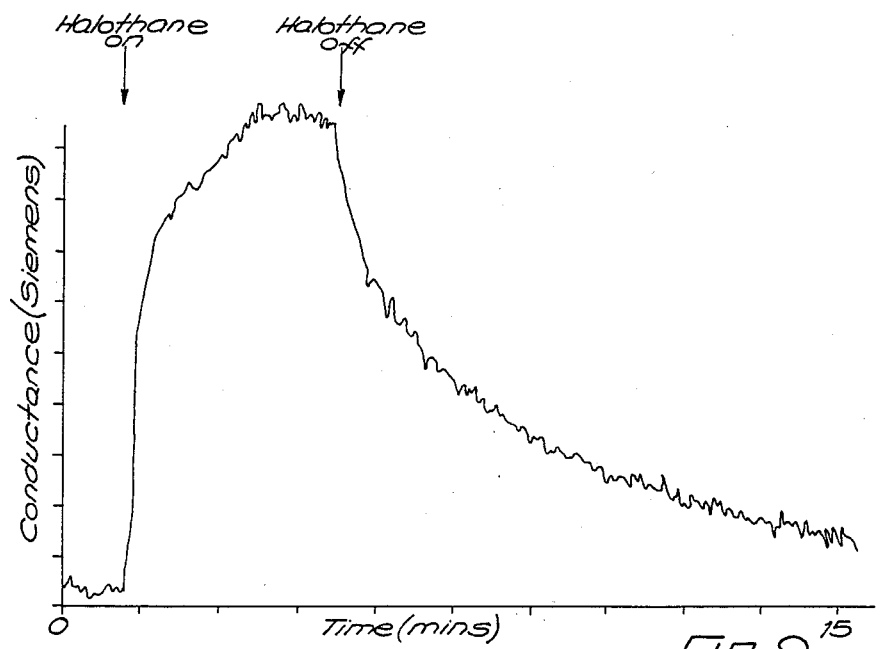
FIG. 9 shows the conductance response of the sensor to 1000 ppm halothane at 93 MHz.
Figure 10:
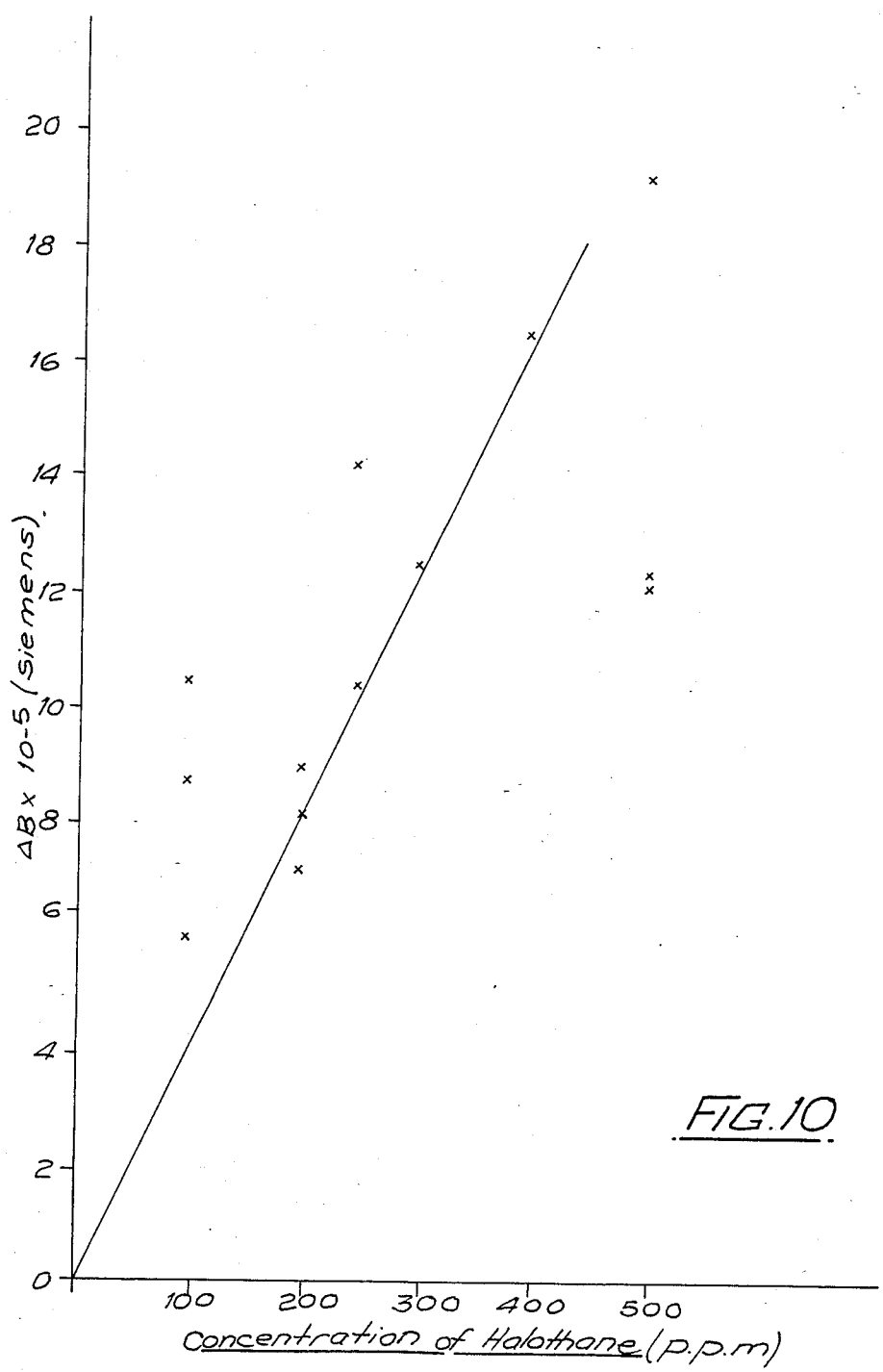
FIG. 10 shows the susceptance response of the sensor to varying halothane concentrations at 393 MHz.

The adsorbent concentration profile through the film appears to be confirmed by measurements of conductance made at two spot frequencies which were monitored over time, while halothane of 1000 ppm V was turned on and then off. FIG. 8 shows the susceptance change over time for a sensor at 393 MHz, whereas, FIG. 9 shows the conductance change at 93 MHz. (The conductance at 493 MHz and susceptance at 93 MHz exhibited negligible change as expected, see FIGS. 6 and 7.)

It will be seen that in each case there was a marked change in each characteristic as soon as the gas supply was switched from the standard ($N_2$) atmosphere to the halothane atmosphere. In the case of the susceptance measurement at 393 MHz, the signal did not change much when the halothane supply was switched off, the signal continuing to fall gradually. However, in the case of the conductance measurement at 93 MHz, the signal started to fall rapidly when the halothane supply was switched off.

FIG. 9 shows a graph of the response of the sensor to varying halothane concentrations, as measured by the change in susceptance at 393 MHz. Although there is an appreciable spread of points on the graph, there is thought to be an overall linear relationship, so that it should be possible to calibrate the device to give an indication of concentration of halothane present.

Figure 11:
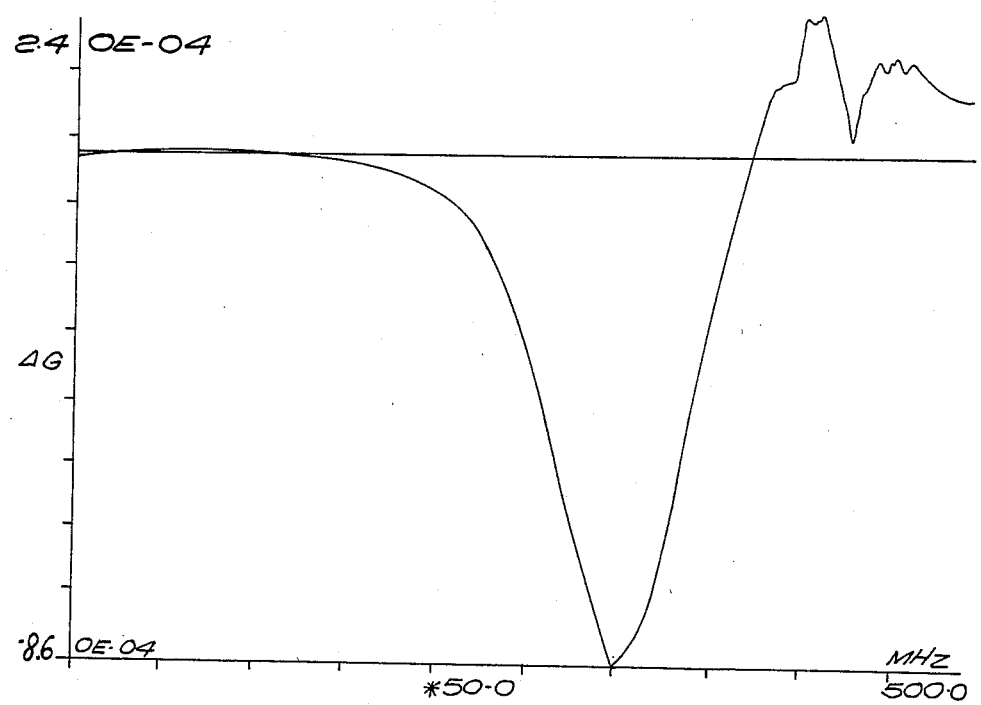
FIGS. 11 and 12 show the difference spectra of the sensor for conductance and susceptance respectively in the presence of ethrane.
Figure 12:
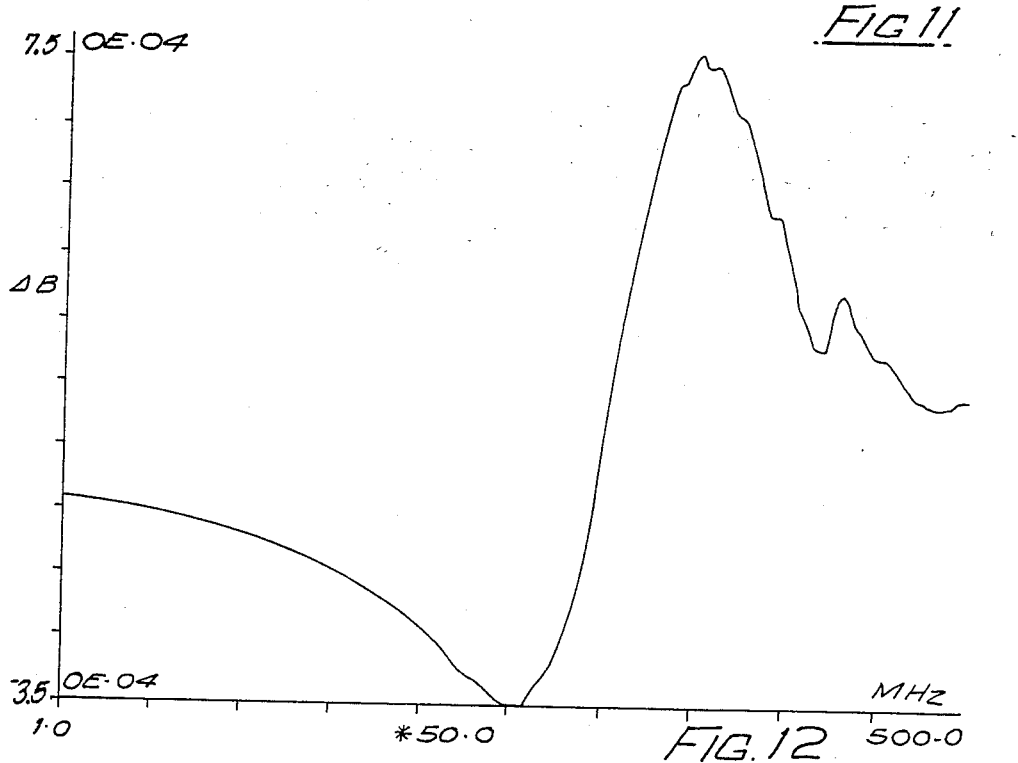

The variation in difference spectra for conductance and susceptance is different for different gases. Thus, FIGS. 11 and 12 correspond to FIGS. 6 and 7, but with the sensor exposed to ethrane rather than halothane. It can be seen that there is a marked difference in the difference spectra of ethrane from that of halothane, so that this method can distinguish the two gases.

Figure 13:
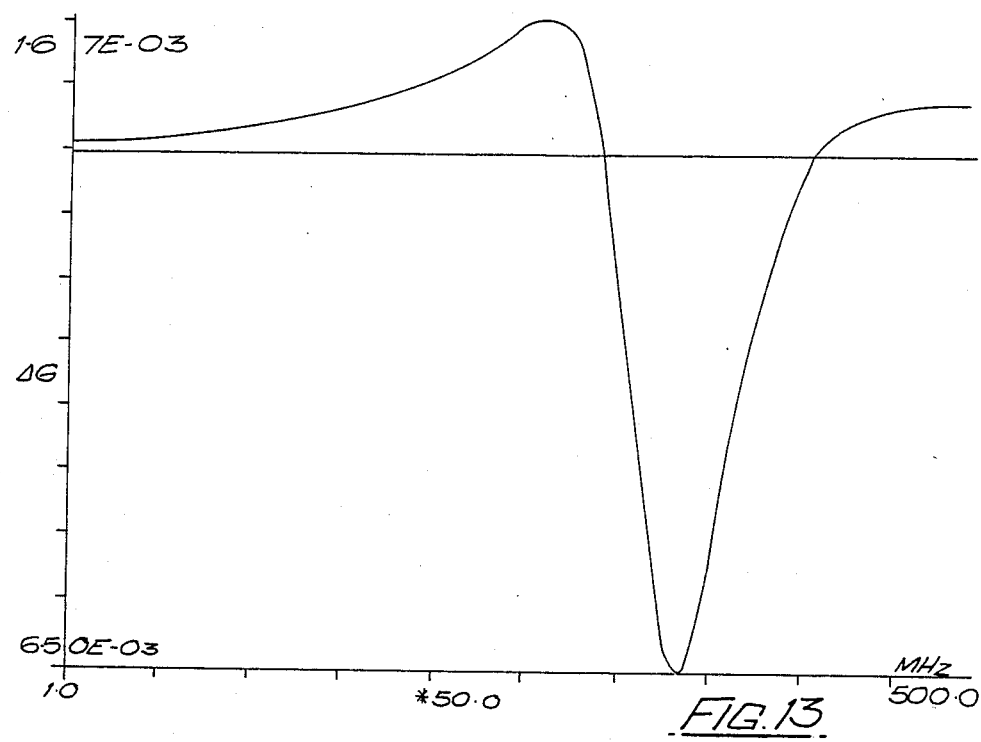
FIGS. 13 and 14 show the difference spectra of the sensor for conductance and susceptance respectively, in the presence of $H_2S$.
Figure 14:
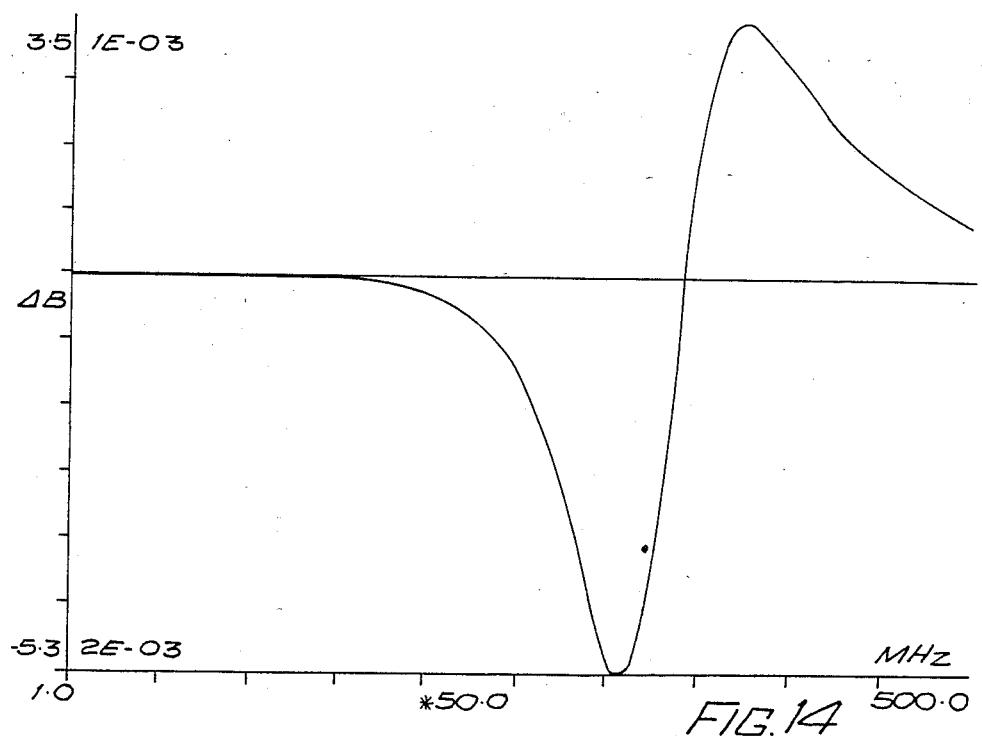

Similarly, FIGS. 13 and 14 show the difference spectra of the impedance characteristics of the sensor in the presence of $H_2S$ and it can be seen that there are differences between these characteristics and the characteristics for halothane and ethrane, enabling this gas to be identified.

Although the above results were obtained using $N_2$ as the reference gas, other reference gases may be used, e.g. dry air.

Each different design and construction of sensor is likely to result in difference impedance spectra and resonant frequencies. This can be used to advantage, inter alia for the following reasons. Very high frequencies are in general not desired, since it gives rise to difficulties in the engineering of the sensor and related equipment. On the other hand, the sensitivity to the presence of gases is likely to be increased as a result of the "skin effect". However, for reasons of construction and electronic circuit design, the highest applied frequency is preferably kept below 500 MHz. The best and most convenient results are therefore likely to be achieved if the characteristic frequencies are in the range 100–500 MHz. However, this is unlikely to be possible in some cases, but it is still possible to adjust the design of the sensor so as to achieve the best compromise.

A device of the present invention can thus be used to detect specific gases, by scanning the sensor with a range of frequencies, and detect the changes in susceptance and conductance, and then analyse these results, perhaps against standard data stored in a microprocessor, to indicate which gas or gases are present.

We claim:

1. A gas sensor for detecting the presence of a gas, the sensor comprising:
   a layer of semiconducting organic polymer;
   means for applying an alternating electric signal to the layer;
   means for varying the frequency of said signal; and
   means for detecting the variation in impedance characteristics of said layer in the presence of said gas.

2. A sensor according to claim 1, wherein said means for detecting the variation comprises,
   means for storing reference impedance variation characteristics, and
   means for comparing said reference variation characteristic with the variation in impedance characteristics of said layer in the presence of said gas to be detected.

3. A sensor according to claim 1, wherein said semiconducting organic polymer is selected from the group consisting of polypyrrole, poly-2-chloroaniline, poly-2-acetonitrile, polyindole, and poly-2-isobutylthiazole.

4. A method of detecting a gas comprising:
   applying an alternating electric signal to a layer of a semiconducting organic polymer, said layer being exposed to said gas;
   varying the frequency of said alternating signal; and
   investigating the variation in impedance characteristics of said layer, thereby to detect said gas.

5. A method according to claim 4, wherein the step of investigating the variation in impedance comprises:
   obtaining a reference variation by determining the variation in impedance characteristic of said layer when exposed to a reference gas, and comparing said reference variation with the variation in impedance characteristic of said layer when exposed to said gas to be detected.

6. A method according to claim 5, wherein the minimum frequency of said frequency variation is 1 MHz.

* * * * *